(12) United States Patent
Van Den Ende et al.

(10) Patent No.: US 10,905,334 B2
(45) Date of Patent: Feb. 2, 2021

(54) ELECTROACTIVE POLYMER SENSORS AND SENSING METHODS

(71) Applicant: KONINKLIJKE PHILIPS N.V., Eindhoven (NL)

(72) Inventors: Daan Anton Van Den Ende, Eindhoven (NL); Mark Thomas Johnson, Eindhoven (NL); Achim Hilgers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 492 days.

(21) Appl. No.: 15/752,622

(22) PCT Filed: Aug. 31, 2016

(86) PCT No.: PCT/EP2016/070520
§ 371 (c)(1),
(2) Date: Feb. 14, 2018

(87) PCT Pub. No.: WO2017/037117
PCT Pub. Date: Mar. 9, 2017

(65) Prior Publication Data
US 2018/0242851 A1    Aug. 30, 2018

(30) Foreign Application Priority Data

Aug. 31, 2015   (EP) ..................................... 15183152
Nov. 10, 2015   (EP) ..................................... 15193821

(51) Int. Cl.
*H01L 41/107*   (2006.01)
*H01L 41/113*   (2006.01)
(Continued)

(52) U.S. Cl.
CPC .............. *A61B 5/01* (2013.01); *A61B 1/0008* (2013.01); *A61B 5/0048* (2013.01);
(Continued)

(58) Field of Classification Search
CPC ....... A16B 5/01; A61B 5/0008; A61B 5/0053; A61B 5/0048; A61B 5/0531;
(Continued)

(56) References Cited

U.S. PATENT DOCUMENTS 4,535,638 A    8/1985 Eernisse et al.
4,547,691 A    10/1985 Valdois et al.
(Continued)

FOREIGN PATENT DOCUMENTS

CN    1643356 A    7/2005
CN    1678891 A    10/2005
(Continued)

OTHER PUBLICATIONS

Jung et al "A Self-Sensing Dielectric Elastomer Actuator" Sensors and Actuators, A 143 (2008) p. 343-351.
(Continued)

*Primary Examiner* — Thomas M Dougherty
(74) *Attorney, Agent, or Firm* — Schott, P.C.

(57) ABSTRACT

The invention provides an electroactive material (preferably electroactive polymer) sensor system, comprising an electroactive material sensor (22) and a control system (28) for performing measurements relating to the impedance of the electroactive material sensor at at least first and second different frequencies. From these measurements a temperature at the sensor and an external pressure or force applied to the sensor can be determined. The sensor can thus be used as a pressure sensor and as a temperature sensor. When used in combination with actuation, an electroactive material actuator with integrated temperature sensing functionality is able to measure the temperature at the exact actuator position, which is always closer than an external thermocouple.

20 Claims, 8 Drawing Sheets

(51) Int. Cl.
| | |
|---|---|
| *H01L 41/09* | (2006.01) |
| *A61B 5/01* | (2006.01) |
| *G01L 1/16* | (2006.01) |
| *H01L 41/04* | (2006.01) |
| *H01L 41/193* | (2006.01) |
| *G01K 7/24* | (2006.01) |
| *A61B 5/00* | (2006.01) |
| *G01L 9/00* | (2006.01) |
| *A61B 1/00* | (2006.01) |
| *A61B 5/053* | (2006.01) |
| *G01K 7/22* | (2006.01) |
| *H01L 41/08* | (2006.01) |
| *A61B 5/08* | (2006.01) |

(52) U.S. Cl.
CPC .......... *A61B 5/0053* (2013.01); *A61B 5/0531* (2013.01); *A61B 5/6843* (2013.01); *A61B 5/7278* (2013.01); *G01K 7/22* (2013.01); *G01K 7/24* (2013.01); *G01L 1/16* (2013.01); *G01L 9/0005* (2013.01); *H01L 41/042* (2013.01); *H01L 41/0825* (2013.01); *H01L 41/1132* (2013.01); *H01L 41/193* (2013.01); *A61B 5/0816* (2013.01); *A61B 2560/0223* (2013.01); *A61B 2560/0252* (2013.01); *H01L 41/0926* (2013.01)

(58) Field of Classification Search
CPC ... A61B 5/6843; A61B 5/7278; A61B 5/0816; A61B 5260/0223; A61B 2560/0252; G10K 7/22; G01K 7/24; G01L 1/16; H01L 41/042; H01L 41/0825; H01L 41/1132; H01L 41/193; H01L 41/0926
USPC .......................................... 310/314–319, 800
See application file for complete search history.

(56) References Cited

U.S. PATENT DOCUMENTS

| | | | |
|---|---|---|---|
| 6,876,135 | B2 | 4/2005 | Pelrine et al. |
| 7,893,965 | B2 | 2/2011 | Heim et al. |
| 8,093,783 | B2 | 1/2012 | Rosenthal et al. |
| 8,604,664 | B2 | 12/2013 | Chiang et al. |
| 2002/0130673 | A1 | 9/2002 | Pelrine et al. |
| 2003/0067245 | A1 | 4/2003 | Pelrine et al. |
| 2003/0214199 | A1 | 11/2003 | Heim et al. |
| 2006/0109538 | A1 | 5/2006 | Mushika et al. |
| 2010/0164324 | A1 | 7/2010 | Kim et al. |
| 2014/0139239 | A1 | 5/2014 | Zachut et al. |
| 2018/0248105 | A1* | 8/2018 | Van Den Ende ... H01L 41/1132 |
| 2019/0286263 | A1* | 9/2019 | Bagheri ................ G06F 3/0446 |
| 2019/0298187 | A1* | 10/2019 | Hendriks .............. G01L 9/0016 |

FOREIGN PATENT DOCUMENTS

| | | |
|---|---|---|
| CN | 101918804 A | 12/2010 |
| CN | 102032970 A | 4/2011 |
| CN | 102239397 A | 11/2011 |
| CN | 102243124 A | 11/2011 |
| CN | 102959378 A | 3/2013 |
| CN | 103124900 A | 5/2013 |
| EP | 0136627 A2 | 4/1985 |
| EP | 1722376 A1 | 11/2006 |
| GB | 2125212 A | 2/1984 |
| JP | 5598314 A | 7/1980 |
| JP | S60-611 B2 | 1/1985 |
| JP | S60-105917 A | 6/1985 |
| JP | H04-1862 B2 | 1/1992 |
| JP | H07-65941 B2 | 7/1995 |
| JP | 2001-099725 A | 4/2001 |
| JP | 2002-022560 A | 1/2002 |
| JP | 2002-022561 A | 1/2002 |
| JP | 4654913 B2 | 3/2011 |
| JP | 5828716 B2 | 12/2015 |
| JP | 6125938 B2 | 5/2017 |
| JP | 6283812 B2 | 2/2018 |
| RU | 2256967 C1 | 7/2005 |
| WO | 2004079832 A2 | 9/2004 |

OTHER PUBLICATIONS

Rosenthal et al "Applications of Dielectric Elastomer EPAM Sensors" Proc. of SPIE, vol. 6534, (2007).

* cited by examiner

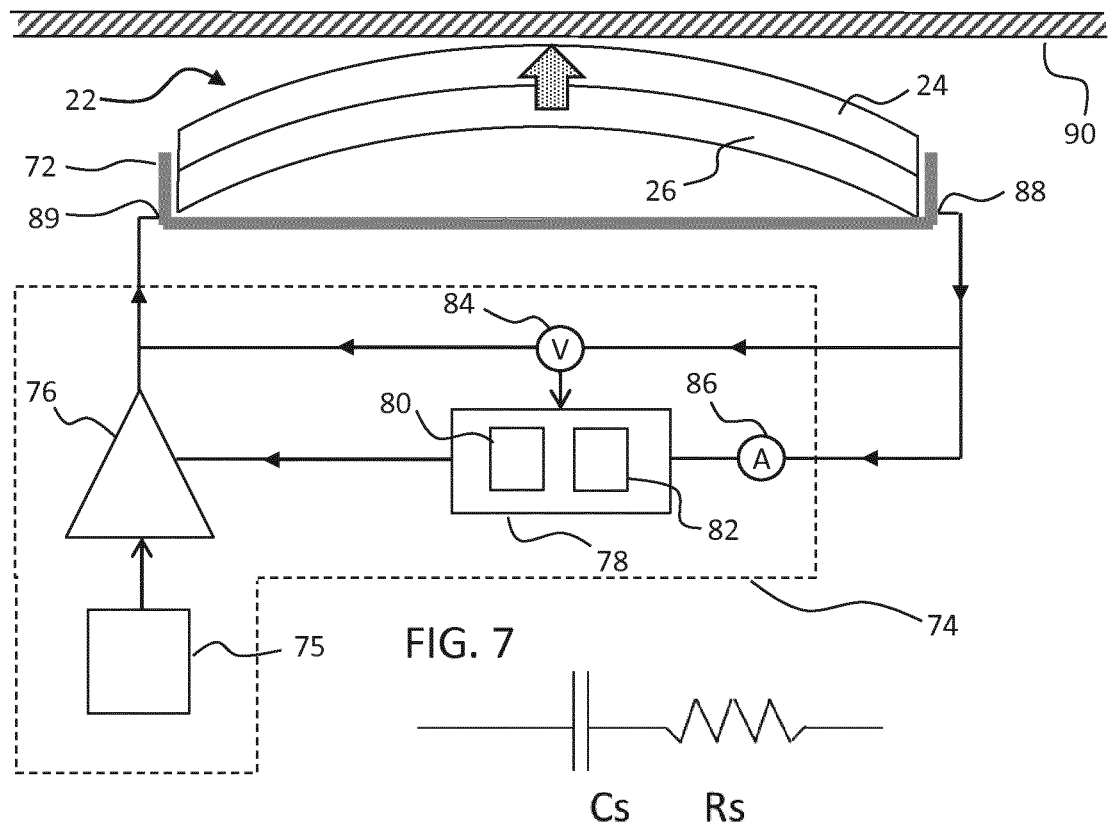
FIG. 7
FIG. 8
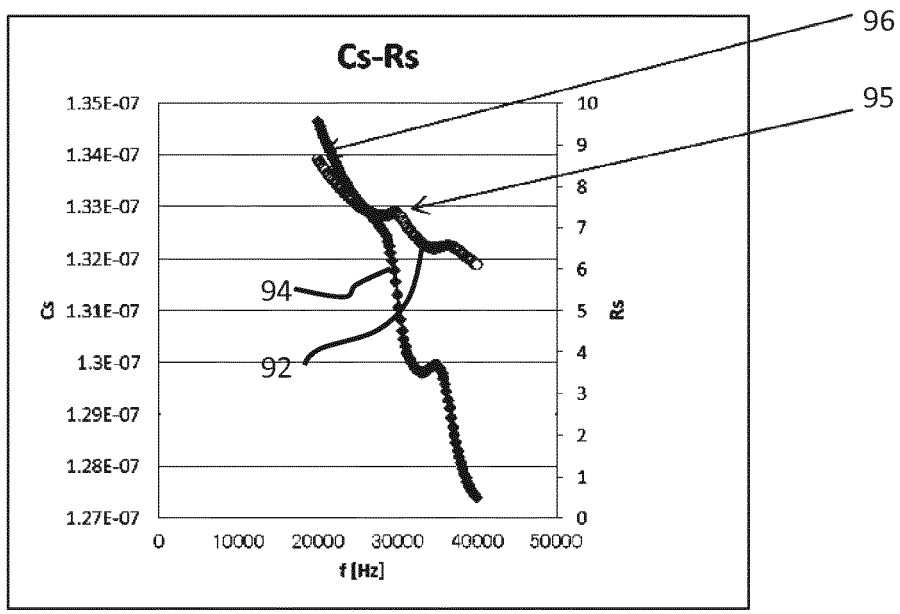
FIG. 9

ELECTROACTIVE POLYMER SENSORS AND SENSING METHODS

CROSS-REFERENCE TO PRIOR APPLICATIONS

This application is the U.S. National Phase application under 35 U.S.C. § 371 of International Application No. PCT/EP2016/070520, filed on Aug. 31, 2016, which claims the benefit of EP Patent Application No. EP 15193821.4, filed on Nov. 10, 2015 and EP Patent Application No. 15183152.6 filed Aug. 31, 2015. These applications are hereby incorporated by reference herein.

FIELD OF THE INVENTION

This invention relates to electroactive polymer sensors and also combined actuators and sensors.

BACKGROUND OF THE INVENTION

Electroactive polymers (EAPs) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP material give rise to applicability to new applications.

An EAP device can be used in any application in which a small amount of movement of a component or feature is desired, based on electric actuation. Similarly, the technology can be used for sensing small movements.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible.

Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nation® and Flemion®.

Another notable subclass of Ionic polymers is Conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

FIGS. 1 and 2 show two possible operating modes for an EAP device.

The device comprises an electroactive polymer layer 14 sandwiched between electrodes 10, 12 on opposite sides of the electroactive polymer layer 14.

FIG. 1 shows a device which is not clamped. A voltage is used to cause the electroactive polymer layer to expand in all directions as shown.

FIG. 2 shows a device which is designed so that the expansion arises only in one direction. The device is supported by a carrier layer 16. A voltage is used to cause the electroactive polymer layer to curve or bow.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

An electroactive polymer structure as described above may be used both for actuation and for sensing. The most prominent sensing mechanisms are based on force measurements and strain detection. Dielectric elastomers, for example, can be easily stretched by an external force. By putting a low voltage on the sensor, the strain can be measured as a function of voltage (the voltage is a function of the area).

Another way of sensing with field driven systems is measuring the capacitance-change directly or measuring changes in electrode resistance as a function of strain.

Piezoelectric and electrostrictive polymer sensors can generate an electric charge in response to applied mechanical stress (given that the amount of crystallinity is high enough to generate a detectable charge). Conjugated polymers can make use of the piezo-ionic effect (mechanical stress leads to exertion of ions). CNTs experience a change of charge on the CNT surface when exposed to stress, which can be measured. It has also been shown that the resistance of CNTs change when in contact with gaseous molecules (e.g. $O_2$, $NO_2$), making CNTs usable as gas detectors.

It has been proposed to combine the sensing and actuation capabilities of EAP devices, for example to provide pressure sensing and actuation functions, typically at separate times. An example is described in US2014/0139239.

US 2014/0139239 discloses an EAP system comprising a sensing circuit, an actuating circuit and a switching circuit. The sensing circuit is adapted to detect a signal from the EAP when it is deformed. Only subsequently does the switching circuit then activate the actuating circuit so that it can generate an actuation based on the sensing input. Hence, sensing and actuation are temporally separated from one another: sensing and actuation occur sequentially, one following on from the other.

This separation of sensing and actuation significantly restricts the range of possible applications for EAP-based sensor-actuators—in particular making it difficult to implement such devices where simultaneous sensing feedback is required during actuation (such as is provided on larger scales by servomechanisms for example).

Temporally simultaneous sensing and actuation is possible by increasing the dimensions of a device to incorporate separate dedicated sensing and actuation regions, with separate sets of electrical connections. However, this is disadvantageous in applications where small form factor is essential.

SUMMARY OF THE INVENTION

The actuation response to a certain voltage of an EAP actuator is temperature dependent. Knowing the temperature at the exact location of the EAP would tremendously benefit the actuation precision. For many applications involving actuators on the skin for example for pressure application, it would be beneficial to simultaneously extract the skin temperature for monitoring (temperature being one of the four primary vital signs).

There is therefore a need for temperature measurement at the location of an EAP actuator with minimum added complexity or space requirement.

This need is at least partially met with the current invention as defined by the independent claims. The dependent claims provide advantageous embodiments.

According to examples in accordance with an aspect of the invention, there is provided an electroactive material sensor system, comprising:

an electroactive material sensor; and a control system for performing measurements of an electrical characteristic which comprises an impedance or an impedance phase angle of the electroactive material sensor at at least first and second different frequencies, wherein the control system is adapted to derive from the measurements a temperature at the electroactive material sensor and an external pressure or force applied to the electroactive polymer sensor.

A direct current signal (DC) signal is meant to include a substantially non alternating electrical signal of either voltage or current. Analogously, an alternating current (AC) signal is meant to include an alternating electrical signal of either or both of voltage and current.

This invention provides a sensor which can be used as a pressure sensor for load sensing e.g. skin contact pressure and as a temperature sensor.

Preferably, the electroactive material sensor comprises a device which functions both as an actuator and as a sensor. Such an actuator with integrated temperature sensing functionality is able to measure the temperature at the exact sensor/actuator position, which is always closer than an external thermocouple. A more space confined solution can be made compared to having a separate temperature sensor.

The measurements enable the pressure or force and temperature on the actuator to be determined, even during actuation. This can be achieved by using the superposition of a drive signal and the measurement signals. The feedback mechanism is for example based on a small amplitude, high frequency electrical signal and this signal is measured alternatingly at two different frequencies to decouple the influence of temperature on the pressure signal.

The first frequency is for example a resonance frequency at which the electrical characteristic has a maximum or minimum value, such as an anti-resonance frequency. The measurement at this frequency is used to determine the external force or pressure.

When a signal is applied at a frequency matching the (undamped) anti-resonance frequency, a sudden mismatch induced by the applied load is for example detected as a consequent drop in impedance as measured across the sensor.

It is alternatively possible to use a driving signal which matches the (undamped) resonance frequency. In this case, the mismatch may be detected as a consequent jump in impedance measured across the sensor. In either case, the high frequency signal, in this way, allows for sensing of external pressure or force applied to the device at the same time as actuation.

The second frequency is a frequency at which the electrical characteristic is constant with respect to load. Instead, it has a variation with temperature, and can thus be used for temperature measurement.

The control system may be adapted to apply a drive signal onto which measurement signals of the first and second frequencies are superposed, wherein the drive signal comprises a DC drive level or an AC drive signal with a frequency below the first and second frequencies.

By superposing a low-amplitude, high frequency sensing signal on top of a higher amplitude primary actuation signal, sensing and actuation functions may be achieved simultaneously, The amplitude of the sensing signal may be significantly less than that of the actuation signal, for example <10% of that of the actuation signal, for example <1% of that of the actuation signal. In this way the deformation response in the electroactive polymer (EAP) structure may be negligible for the sensing signal compared to that stimulated by the actuation signal. Hence precision, accuracy and stability of the device as an actuator is not compromised.

The first drive signal (an actuation signal) may be a DC signal (although with a DC level which varies in dependence on the actuation desired), or may have an alternating amplitude (AC signal). The frequency of the actuation signal in the latter case may also be significantly less than that of the sensing signal, for example at least two orders of magnitude less, in order to avoid interference of the actuator signal with the measurement signal.

This enables simultaneous sensing and actuation. The two, different frequency, measurement signals may be applied in sequence. Alternatively the different frequency measurements may be superimposed, since the size of the off-resonance frequency can be freely chosen.

The system may comprise an array of sensors, wherein at least some of the sensor have different first frequencies. In this way, different sensors can be placed into the sensing mode by application of a suitable measurement signal. For example, each of the plurality may have a different size and/or shape and/or geometry, thereby providing a different resonant frequency. The different first frequencies may be detectable in the measured impedance signals and this for example used to determine to which sensor in the array or assembly in particular any load is being applied. Hence, a more precise determination of the position of an applied pressure might be determinable.

The controller may be adapted to modify the derived external force or pressure based on the derived temperature. Thus, the temperature signal may not only be a source of useful information, but it may also be used to provide temperature compensation for the force or pressure sensing function.

The electrical characteristic preferably comprises an impedance value such as a series resistance.

The invention will work with electroactive materials in general. However, particularly useful materials will be organic electroactive materials and/or polymeric electroactive materials. These have the electroactive characteristics, a suitable temperature dependence and also have ease of processing for them to be integrated in devices such as in body lumen (e.g. catheters). The electroactive Material (polymer) may comprise a relaxor ferroelectric. By way of non-limiting example of such polymeric materials, terpolymers (i.e. PVDF-TrFE-CFE or PVDF-TrFE-CTFE) relaxor ferroelectrics may be used. They are non-ferroelectric in the absence of an applied field, meaning that there is no electromechanical coupling when no drive signal is applied. When a DC bias signal is applied, for example, the electromagnetic coupling becomes non-zero. Relaxor ferroelectrics provide larger magnitudes of actuation deformation, and greater sensing sensitivity compared with other known EAP materials. However, the device is not limited to the use of Relaxor ferroelectrics, and piezoelectric EAP materials (such as, by way of example only, PVDF or PVDF-TrFE), may also for example be used in embodiments. Other examples will be either known to the person skilled in the art or are described herein below. The materials choices will also hold for the method of the invention.

Examples in accordance with a second aspect of the invention provide a sensing method using an electroactive material material sensor, comprising:

performing measurements of an electrical characteristic of the electroactive material sensor at at least first and second different frequencies; and deriving from the measurements a temperature at the sensor and an external pressure or force applied to the sensor.

This method may be used as a sensing method or it may be used during actuation so that it comprises a combined sensing and actuation method, for example using a superimposed high frequency AC signal which is used to measure the electromechanical response of the electroactive material (i.e. as represented by the electrical characteristic) at two particular frequencies. One of these is preferably a characteristic electromechanical resonance frequency used for the force or pressure sensing. The first frequency is for example a resonance frequency, such as an anti-resonance frequency, at which the electrical characteristic has a maximum or minimum value.

The second frequency is preferably outside the resonance/anti-resonance range and it used for the temperature measurement. The second frequency is for example a frequency at which the electrical characteristic is constant with respect to the load applied.

The method may comprise applying an actuator drive signal and superposing measurement signals of the first and second frequencies, wherein the actuator drive signal comprises a DC drive level or an AC drive signal with a frequency below the first and second frequencies. The derived external force or pressure may be modified based on the derived temperature.

The first and second frequencies may be obtained by performing a calibration operation, wherein the calibration operation comprises applying a first frequency sweep with no actuation signal and applying a second frequency sweep with an actuation signal.

BRIEF DESCRIPTION OF THE DRAWINGS

Examples of the invention will now be described in detail with reference to the accompanying drawings, in which:

FIG. 7 shows the electroactive polymer device of FIG. 3 in more detail;

FIG. 8 shows one equivalent circuit of an EAP device;

FIG. 9 shows changes in resistance and capacitance with frequency;

DETAILED DESCRIPTION OF THE EMBODIMENTS

The invention provides an electroactive polymer sensor system, comprising an electroactive polymer sensor and a control system for performing measurements of relating to the impedance of the electroactive polymer sensor at at least first and second different frequencies. From these measurements a temperature at the sensor and an external pressure or force applied to the sensor can be determined. The EAP sensor can thus be used as a pressure sensor and as a temperature sensor. When used in combination with actuation, an EAP actuator with integrated temperature sensing functionality is able to measure the temperature at the exact EAP position, which is always closer than an external thermocouple.

Figure 1:
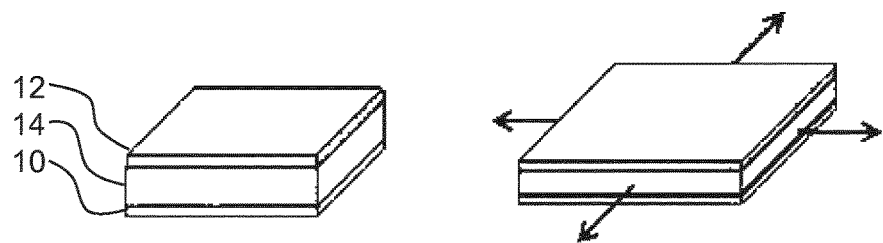
FIG. 1 shows a known electroactive polymer device which is not clamped.
Figure 2:
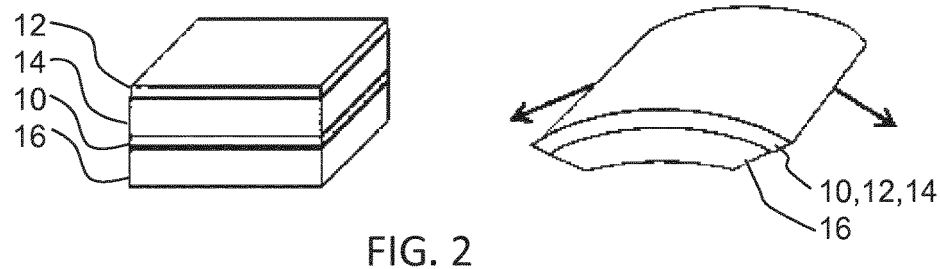
FIG. 2 shows a known electroactive polymer device which is constrained by a backing layer.
Figure 3:
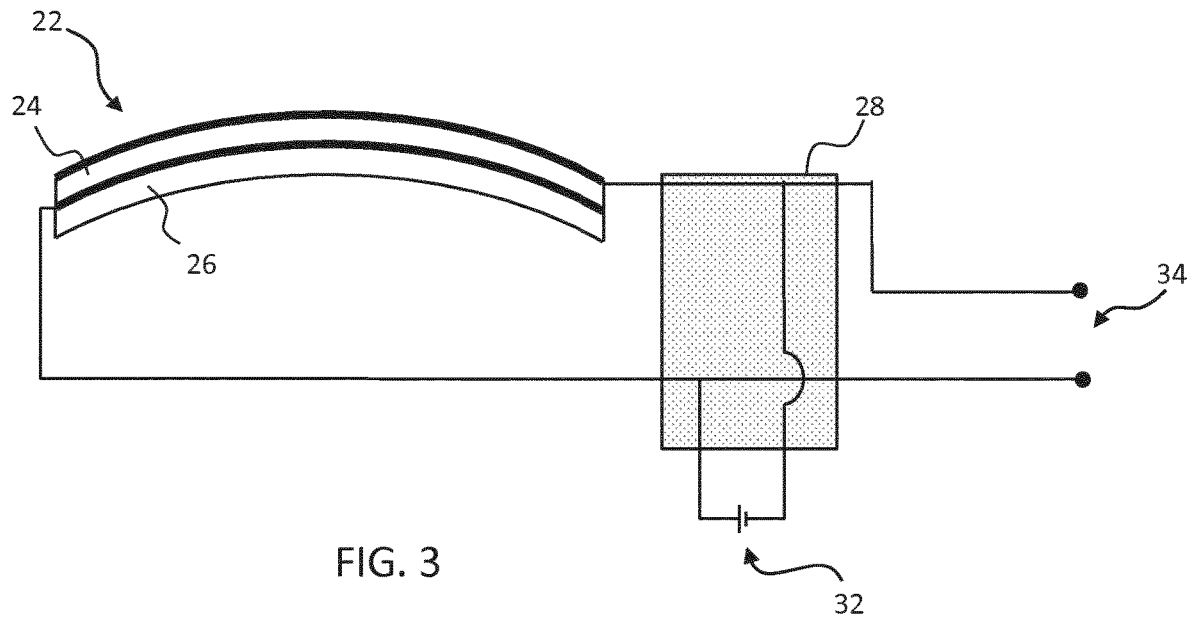
FIG. 3 shows a first example of electroactive polymer device.

In FIG. 3 is shown a schematic illustration of a simple first arrangement for an actuator and sensor device according to embodiments of the invention. An EAP actuator 22, comprising an upper EAP material layer 24 disposed atop a lower carrier layer 26 is electrically connected via a signal processing element 28 with first (DC) drive signal input 32 and second (AC) drive signal input 34. The first drive signal input 32 is for application of a (relative) high power actuation drive signal. The second signal input 34 is for application of a (relative) low power alternating sensing signal, and in particular at two different frequencies, as will be discussed below. The signal processing element superposes the first and second drive signals to form a third combined drive signal, which is then applied across the device.

The signal processing element may in examples comprise a number of component elements for performing, for example, signal analysis functions, signal coupling and decoupling functions and/or signal generation functions. In the latter case, the first and second drive signal inputs 32 and 34 may be encompassed within the processing unit 28 itself, the processing unit comprising elements for generating AC and/or DC signals and, in some cases, elements for analysis of electrical parameters of one or both signals.

The electrical connections of the arrangement of FIG. 3 are shown connected to electrodes at the top and bottom planar surfaces of the EAP layer structure for example. Flexible electrode arrangements may be used for this purpose. Application of DC and/or AC voltages to the electrodes allows the generation of an electric field across the EAP layer which stimulates a corresponding deformation.

Although the first drive signal input 32 in the arrangement of FIG. 3 comprises a DC input, in alternative arrangements, this input may comprise an AC drive signal input. In either case, the relative power of the actuation drive signal significantly exceeds that of the applied sensing signal. In the case that both signals comprise AC signals, the maximal amplitude of the sensing signal (applied at 34) may be less than 10% of the maximal amplitude of the actuation drive signal (applied at 32), for example less than 1% of the maximal amplitude of the actuation drive signal. In the case that the sensing signal comprises an AC signal, and the actuation signal comprises a fixed amplitude DC bias signal, the maximal amplitude of the AC signal may be less than 10% of the fixed amplitude of the DC bias signal, for example less than 1% of the fixed amplitude of the DC bias signal.

For the example of FIG. 3, the third combined signal generated by the signal processing element 28 comprises a high frequency, low-amplitude AC signal superposed atop a high amplitude DC bias signal.

As described in preceding sections, the application of a DC bias of sufficient amplitude across a layer of electroactive polymer stimulates an expansion of the polymer layer. If the layer is coupled with a passive carrier layer 26 the expansion of the polymer results in a deformation, for example a bending or warping, of the overall structure, which may be used to provide an actuation force. In FIG. 3, the actuator structure 22 is shown in an 'active' or 'actuated' state, wherein a DC bias is being applied of sufficient magnitude to cause a deformation of the structure. As is well known, the extent of expansion varies in relation to the magnitude of the electric field/electric current applied across the device. Hence by varying the amplitude of the DC bias, deformation of differing degrees/extent may be induced, and differing magnitudes of actuation forces applied (or differing amounts of actuation work done, for example).

The high frequency AC signal superposed atop the DC bias also stimulates a mechanical deformation response in the material, but a deformation response which is periodic, rather than fixed (i.e. an oscillation). However, since the maximal amplitude of the high frequency signal is significantly lower than the amplitude of the DC bias signal (for example two orders of magnitude lower than that of the DC bias signal, for example, 1% of that of the DC signal), the corresponding displacement amplitude of the stimulated deformation is effectively negligible compared to the primary actuation displacement. Hence the accuracy and stability of the actuation is not affected by the superposition of the sensing signal.

The overlay of a low-amplitude oscillation signal on top of the DC bias allows for an electrical feedback mechanism to be incorporated within the primary actuator driving mechanism itself. At certain frequencies, in particular at frequencies which match or are harmonic with the mechanical resonant frequency of the actuator structure 22, a small mechanical standing wave is established in the material of the actuator. This in turn influences the electrical characteristics of the material. When the sensing signal is driven at the resonance frequency of the material, the corresponding impedance of the material is lower (compared to when driven at non-resonance) due to the mechanical vibration being in-phase with the electrical driving signal.

The mechanical resonance frequency of a structure is the frequency at which a structure will naturally tend to oscillate, upon being displaced from its equilibrium position, and is determined by intrinsic structural properties of the structure (e.g. geometry, size, shape, thickness etc.). The mechanical oscillation of the EAP structure will not necessarily follow the drive frequency of the electrical signal applied to it, but will tend to fall back to its natural resonance frequency, with the drive frequency interfering with that oscillation either constructively or destructively, depending upon the degree to which the driving frequency is either out of phase or in phase with the natural oscillating frequency (resonance frequency).

When the high-frequency signal is driven at the anti-resonance frequency of the EAP structure (i.e. the first harmonic of the resonance frequency), the impedance of the EAP is higher, due to the mechanical vibration of the material being out of phase with the oscillation of the drive signal (the electrically induced mechanical strains are out of phase with the electrical excitation). In other words, whenever, for instance, a positive current is being applied to the EAP by the drive signal, the out of phase mechanical strains are at the same moment inducing a current in the opposite direction (i.e. out of phase behavior). In the ideal (model) case these opposing currents cancel each other out, and no current can flow at all (i.e. infinite impedance), but in real-world scenarios no full cancellation occurs and this effect is measured as an (effective) higher resistance of the electrical current (i.e. higher impedance). In particular, when the signal is driven at the anti-resonance frequency of the actuator material, the impedance of the EAP is at a maximum.

The relationship may be further understood by considering equation (1) below. The impedance of an ideal EAP at resonance and anti-resonance depends on the particular type or mode of deformation. It is most common to bring the EAP into lateral resonance (i.e. length or width). The impedance of the EAP is governed by the dielectric properties of the material and the electromechanical coupling and electrical and mechanical losses. For simplicity, when ignoring the electrical and mechanical losses, for an EAP with length l, width w and thickness t, deforming in lateral extension, the impedance of the EAP is given by:

$$Z(\omega) = \cfrac{1}{i\omega \cfrac{lw}{t}\varepsilon_{33}^T \left[(k_{31})^2 \cfrac{\tan\left(\cfrac{\omega l}{2}(\rho s_{11}^E)^{1/2}\right)}{\cfrac{\omega l}{2}(\rho s_{11}^E)^{1/2}\gamma\alpha^{(E)}} + 1 - (k_{31})^2\right]}$$

where $\varepsilon_{33}^T$ is the dielectric constant, $k_{31}$ is the lateral electromechanical coupling factor, p is the density of the EAP and $s_{11}^E$ is the compliance in the lateral direction. At anti-resonance frequency, $$\omega_a, \tan\left(\frac{\omega l}{2}(\rho s_{11}^E)^{1/2}\right) = 0 \text{ and } Z \text{ is highest.}$$

A real EAP has losses and can be modeled or represented by a capacitor with a resistor in series, the resistance of which is greatest at the anti-resonance frequency. In the descriptions which follow, therefore, 'impedance' and 'series resistance' (Rs) may be used interchangeably with reference to the device. However, series resistance is to be understood in this context as referring simply to a model in which the actuator/sensor is represented electronically by a capacitor in series with a resistor, having resistance Rs.

In consequence of the above-described relationship between impedance and resonance, when the drive signal is being driven at the anti-resonance frequency, any small deviations which occur in its frequency away from anti-resonance will be detectable in a corresponding sharp drop-off the in measurable impedance of the EAP structure 22. It is this physical effect which allows mechanical sensing to be achieved. Application of load (i.e. pressure or force) to the EAP structure results in a dampening of any resonance effects which are occurring within the material. If the drive signal is oscillating at the anti-resonance or resonance frequency of the material when the load is applied, the dampening effect will be identifiable within real-time measurements of the EAP impedance (i.e. series resistance Rs), as the sudden cessation of resonance will effect a consequent sharp decline in the impedance. Hence by monitoring the impedance of the structure over time, while the actuator is in operation (for example by monitoring the voltage and current of the high-frequency signal over time), pressures and loads applied to the structure can be sensed, and in some cases quantitatively measured (as will be described below).

The link between impedance on the one hand, and the phase difference between the electrical drive frequency of the signal and the mechanical oscillating frequency of the material on the other, allows for highly sensitive measurement of applied mechanical forces to the EAP to be achieved through the monitoring of electrical properties of the drive signal only. This hence provides a highly simple, straightforward and efficient means for achieving simultaneous actuation and sensing using a single EAP device. Moreover, embodiments of the invention allow simultaneous sensing and actuation over the same region of EAP structure (i.e. spatially simultaneous sensing and actuation). This means that a device performing both functions can be made with a much smaller form factor, without sacrificing sensitivity or resolution of sensing for example. Moreover, only a single set of connections is require to be provided to the device (as opposed to two or more sets of connections, one for each dedicated sensing or actuation region) which is advantageous in terms of cost and reduced complexity, and in cases where watertight connections are required for example (for instance in shaving/catheters/oral healthcare) and/or where an array of actuators/sensors is to be constructed.

Furthermore, by suitable selection of sensing signals and with suitable signal processing, the sensing provides temperature as well as load sensing. In particular, measurement signals of least first and second different frequencies are generated, and the signal processing element 28 is used to measure one or more electrical characteristics of the actuator 30 at the two measurement frequencies. In this way, a temperature at the actuator and an external pressure or force applied to the actuator, are both determined.

The frequency of the high-frequency sensing signals may each typically be in the range of 1 kHz to 1 MHz, depending on the particular geometry of the actuator. Note that in the case that the actuator drive signal comprises an AC drive signal, the frequency of this signal is significantly lower than that of the alternating sensing signal. The (low frequency)

actuation voltage in this case may for example be at least two orders of magnitude lower than the high frequency signal voltage, to avoid interference of the actuator signal with the measurement signal.

As explained above, at the anti-resonance frequency, the measured impedance is higher due to the out-of-phase mechanical vibration. In particular, the series resistance (Rs) of the actuator is at a local maximum at this frequency. In implementation, this frequency is used as a first one of the measurement frequencies. Another measurement frequency is defined which is outside the electromechanical coupling frequency range, and this is used as the second measurement frequency.

Figure 4:
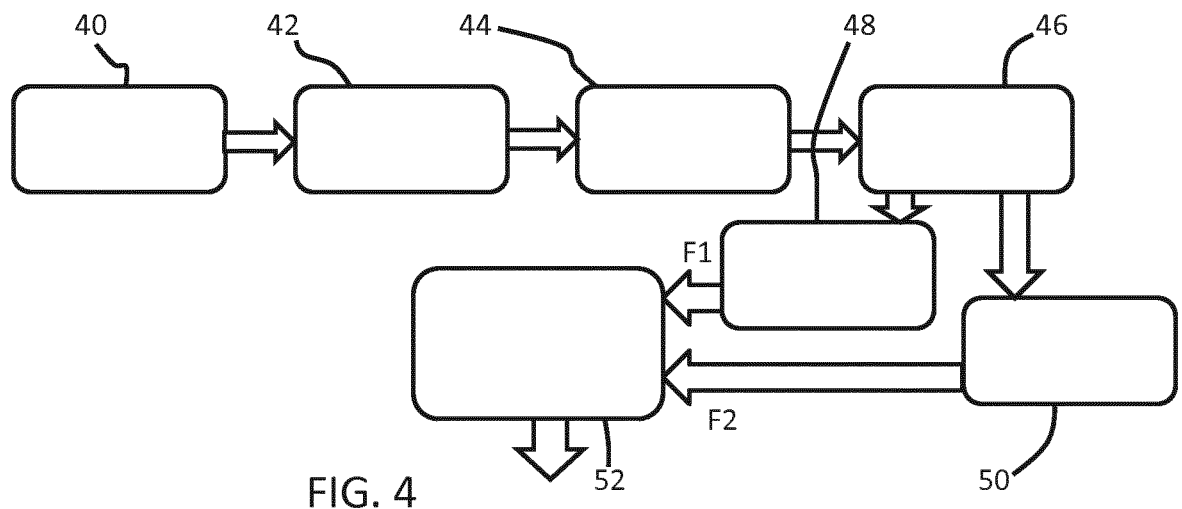
FIG. 4 shows a calibration method.

A calibration process may be used to determine the frequencies to be used and for determining a relationship between measured resistance and applied load at said determined resonant frequency. FIG. 4 shows one example.

A first frequency sweep 40 is performed, at an applied DC bias of 0V, and resistance responses measured. The equivalent series resistance of the actuator is thereby measured at the different frequencies to obtain an impedance versus frequency function, with no actuation signal present.

A fixed DC bias is then applied in step 42, preferably corresponding to a desired actuation state of the device. At this time, there may be no load applied to the device.

A second frequency sweep is then performed in step 44 at the fixed non-zero DC bias, and corresponding resistance values recorded. The equivalent series resistance of the actuator is again measured at the different frequencies to obtain an impedance versus frequency function, with an actuation signal present.

The results of the two sweeps are then compared in step 46 to determine the difference in the obtained resistance values for each across the range of frequencies.

In step 48, the first frequency for which the measured resistance values differ by the greatest amount is determined and the anti-resonance frequency thereby directly identified.

In step 50, the second measurement frequency is defined. It is a frequency at which the difference is negligible. Thus, it is a frequency at which the electrical characteristic is constant with respect to load.

Note that steps 40 to 50 may be in some cases repeated for as many DC voltages as are desired, for example to gather data relating to a plurality of different actuation positions, in the case that variable actuation extent is to be employed in the operation of the device.

For a sensor-only device, there will be a single actuation, which brings the sensor into an actuated state at which it is ready to perform sensing. Thus, only one driven calibration is needed.

The sensor could for example be set into a position and used from then on as a sensor only. This may be considered to correspond to a single actuation level used for making multiple sensing measurements. A sensing function may be used with a DC bias within a certain range. However, this range may include DC bias voltages for which there is no physical actuation, but there is nevertheless sensitivity to an applied load. In particular, the actuation curve (actuation versus applied voltage) is non-linear with a threshold voltage below which physical actuation does not start. In this case, the sensing function is enabled even without physical deformation, although the sensed signal will be smaller than for a larger DC bias.

Figure 5:
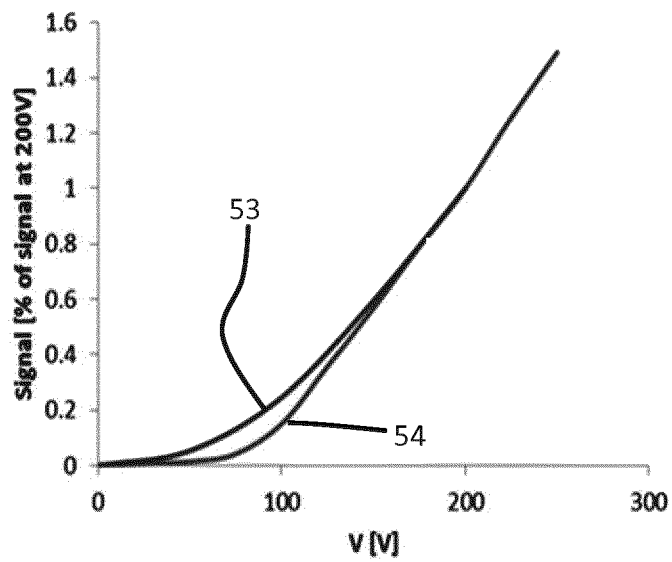
FIG. 5 is a graph to show how a sensor only function may be used.

FIG. 5 shows a plot of the signal strength for sensing a fixed load at different actuation voltages, as plot 53. Plot 54 shows the actuation level for those actuation voltages (with arbitrary scale). It can be seen that the sensitivity increases more rapidly than the actuation for voltages increasing from an initial zero level.

A typical DC bias range for sensing only may for example be in the range 40V to 50V, or 40 to 75V, where sensitivity is above zero but actuation is still zero or close to zero (respectively).

In step 52 of FIG. 4, calibration data for the impedance value is derived, in the form of series resistance across the device versus applied load, for a fixed DC bias voltage, and a fixed AC signal frequency—equal to the anti-resonance first frequency.

Furthermore, an impedance value is obtained for each temperature in a range of interest and for each possible actuation signal. At the second frequency, an impedance value is obtained for each temperature in a range of interest, for each possible actuation signal, and for each possible load.

Thus, in step 52, there multiple measurements at different temperatures and with different load applied. This calibration process takes place in the factory and a lookup table is generated for Rs at frequency 1 and frequency 2 for variable applied load and temperature. At each temperature, the full range of loads is measured. This lookup table is used as reference during use.

In this way, the actuator is calibrated for the impedance versus load for each applied voltage (if there are multiple applied voltages) and at each temperature point within the temperature range.

During actuation, the measured impedance value at the first frequency in combination with the applied voltage gives a measure for the force on the actuator and the impedance value at the second frequency gives a measure of the temperature of the EAP actuator. The displacement amplitude of the high frequency (sensor) signal is negligible compared to the actuation displacement, so it will not interfere with the actuation in terms of accuracy or stability.

Figure 6:
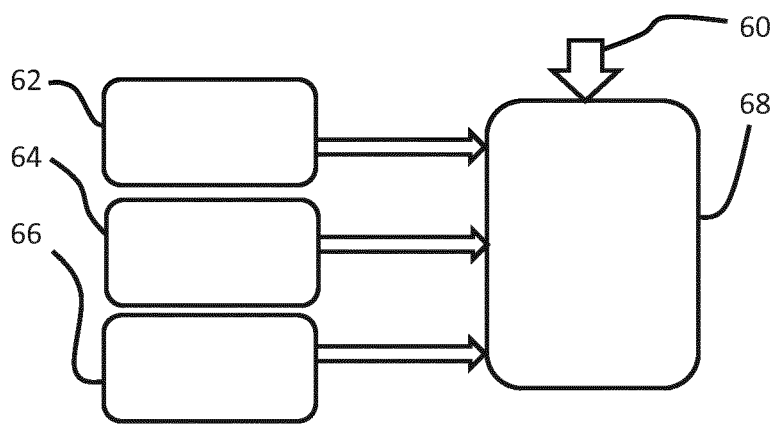
FIG. 6 shows a sensing method for use after the calibration.

FIG. 6 shows the method which is used during use of the actuator. The calibration data is received as represented by arrow 60. Step 62 involves measuring the impedance at the first calibration frequency. This is used for load (i.e. pressure or force) sensing. Step 64 involves measuring the impedance at the second calibration frequency. This is used for temperature sensing.

During these measurements, the higher amplitude actuation signal is applied in step 66. It will be a constant for a sensor only implementation or it will be variable for a sensor and actuator. Step 68 involves deriving the load on the actuator and the temperature.

These two parameters may be provided as separate outputs from the system. Alternatively, the temperature information may be used internally by the system to provide temperature compensation of the sensed load.

A first example will be described in more detail, based on a DC actuation signal, as shown in FIG. 7.

As explained above, the EAP actuator 22 has EAP material layer 24 and passive carrier layer 26 and is held within a housing 72, and is electrically coupled with a signal drive mechanism 74. The drive mechanism in the example of FIG. 7 comprises both signal generation elements (drive elements) and signal processing and analysis elements (sensor elements).

An actuator control element 75 generates a high-amplitude actuator drive signal (for example a fixed DC bias voltage) which is transmitted to a signal amplifier device 76. A sensor control element 78 comprises both a driver element 80 for generating the sensor signals, and a processing element 82 for analyzing electrical properties of the sensor signals after passage across the actuator. To this end, the drive mechanism 74 further comprises a voltmeter 84, connected across the EAP actuator 22, and an ammeter 86 connected in series between the outgoing electrical terminal 88 of the actuator and the sensor control element 78. The voltmeter 74 and ammeter 76 are both signally connected with the sensor control element 78, such that data generated by them may be utilized by the processor 82 in order to determine an impedance of the actuator 22 (that is, the equivalent series resistance Rs where the device is modeled as an ideal capacitor with a resistor in series, i.e. the real part of the complex impedance).

Drive signals generated by the actuator control element 75 and sensor control element 78 are superposed by the amplifier element 76, either in advance of their combined amplification, or after their independent amplification. In some examples, the amplifier element 76 might be replaced simply by a combiner. In this case actuator control element 75 and sensor control element 78 may be adapted to amplify their generated actuation and sensing signals locally, in advance of outputting them to the combiner.

The combined drive signal is then transmitted to the ingoing terminal 89 of the EAP actuator 22. The high amplitude DC component of the combined drive signal stimulates a deformation response in the actuator.

For the most reproducible (i.e. reliable/accurate) results, the EAP may be clamped in position. For example, the actuator may be clamped within housing 72, and the housing then positioned so as to align the device with the target actuation area.

For illustration, a target actuation area 90 is shown in FIG. 7, wherein the actuator is deformed by the DC drive signal to apply pressure to the target area. In examples, the target area might for example comprise a region of a person's skin, for instance, such that pressure may both be applied to the skin, but force and temperature applied upon the actuator by the skin simultaneously sensed by the device (e.g. it can be sensed how hard the user is pressing the actuator-containing device to their skin).

In some examples, an (optional) force transfer mechanism may additionally be provided, for delivery of forces in a controlled way to or from the actuator surface.

The low-amplitude AC component of the drive signal stimulates a low amplitude periodic response in the EAP layer 24, for example oscillating the structure at its resonant or anti-resonant frequency.

The voltage of the combined drive signal and the resulting current are fed to sensor control element 78. Typically the AC currents may be in the range of 0.1 mA to 1 mA, but may be up to 10 mA. Higher currents may cause too much heating.

In some cases, the drive mechanism 74 may further comprise one or more signal decoupling elements, for example a high pass filter, for the purpose of isolating high-frequency components for analysis by the processing element 82 of sensor control element 78.

The processing element 82 of sensor control element 78 may use measurements provided by voltmeter 84 and ammeter 86 in order to determine a series resistance across the actuator, as experienced by the applied drive signal(s). The series resistance may be determined in real time, and monitored for example for sudden changes in resistance, which as explained above, may be used to indicate the presence and magnitude of loads and pressures applied to the actuator 22.

The EAP actuator has an approximate equivalent circuit of a series capacitor Cs and resistor Rs as shown in FIG. 8.

The sweep explained above, which is used to determine the anti-resonance frequency (the point of highest sensitivity), is shown in FIG. 9.

The measured series resistance (in Ohms) is shown on one y-axis, the measured capacitance (in Farads) is shown on another y-axis and the sensor signal frequency (in Hz) on the x-axis.

Plot 92 is the resistance and plot 94 is the capacitance. For this sample, a frequency of around 29.8 kHz is determined as the anti-resonance frequency as a result of the local resistance peak shown as 95. A frequency away from the point is selected as the second frequency, such as point 96 at 20 kHz. The plots are for a bias voltage of 200V.

Figure 10:
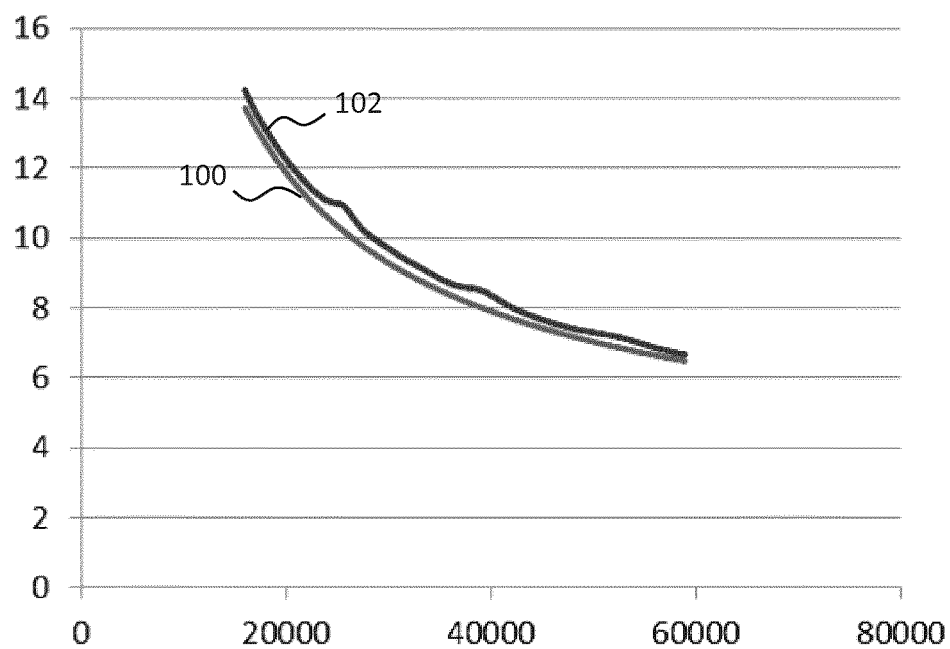
FIG. 10 shows changes in with frequency for two different actuation voltages.

As explained above, the peaks are most easily determined by comparing plots. FIG. 10 shows a resistance measurement for a 0V sweep as plot 100 (which shows no variation about the primary curve which reflects simply a capacitive complex impedance function) as the AC frequency is varied. At 0V bias, there is little or no coupling, and hence zero (or unmeasurably small) deformation response in the material to the AC signal. The 0V bias sweep hence provides a convenient baseline against which to compare an AC frequency sweep at a higher (actuation inducing) DC voltage. Plot 120 is the sweep with an applied DC bias.

The anti-resonant frequency of the device may be identified by finding the AC frequency for which the difference between the measured resistance values for the two DC voltages is the greatest.

Figure 11:
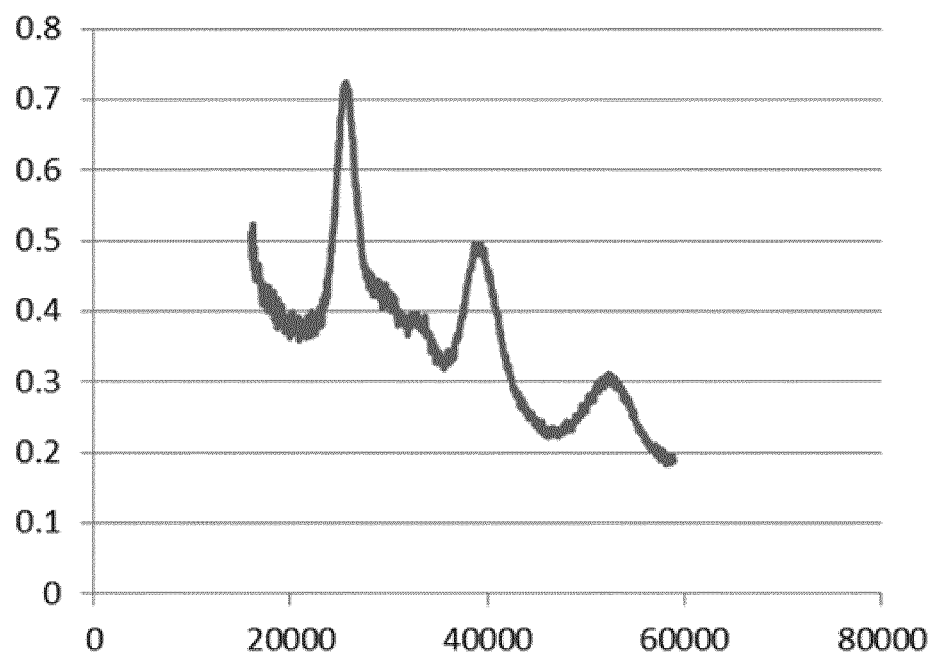
FIG. 11 shows how the difference between the plots of FIG. 10 can be used to identify resonance frequencies.

In FIG. 11 is illustrated more clearly the difference between the two signal traces, with difference in measured resistance on the y-axis and corresponding sensor signal frequency on the x-axis. The two larger jumps in resistance are clearly visible in this graph, with the larger of the two being the jump occurring at anti-resonance.

Although a DC bias of 0V is used for the first sweep in this example, in alternative examples a different (non-zero) first bias might be used. In this case, depending on the magnitude of the first voltage, the first sweep may indicate variations or peaks about the central curve. However, the anti-resonance frequency may still be found by identifying the frequency for which the difference between the measured resistance values for the two DC voltages is the greatest.

Figure 12:
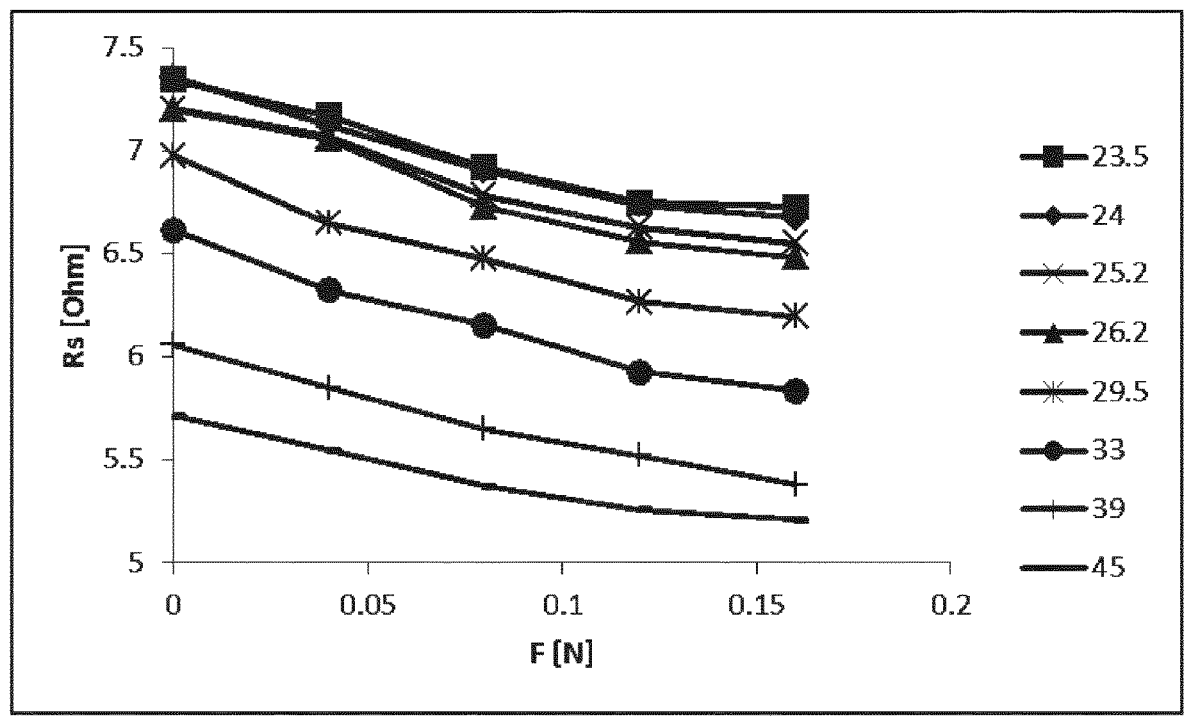
FIG. 12 shows the dependency the impedance on the load for different temperatures at resonance.

The load also has an influence on the series resistance of the actuator, by damping the resonance-anti resonance behavior. This is shown in FIG. 12 which plots the resistance Rs at anti-resonance measured on an actuator with 200V bias against the load. Each plot is for a different temperature, and the temperature offset drift is visible.

Figure 13:
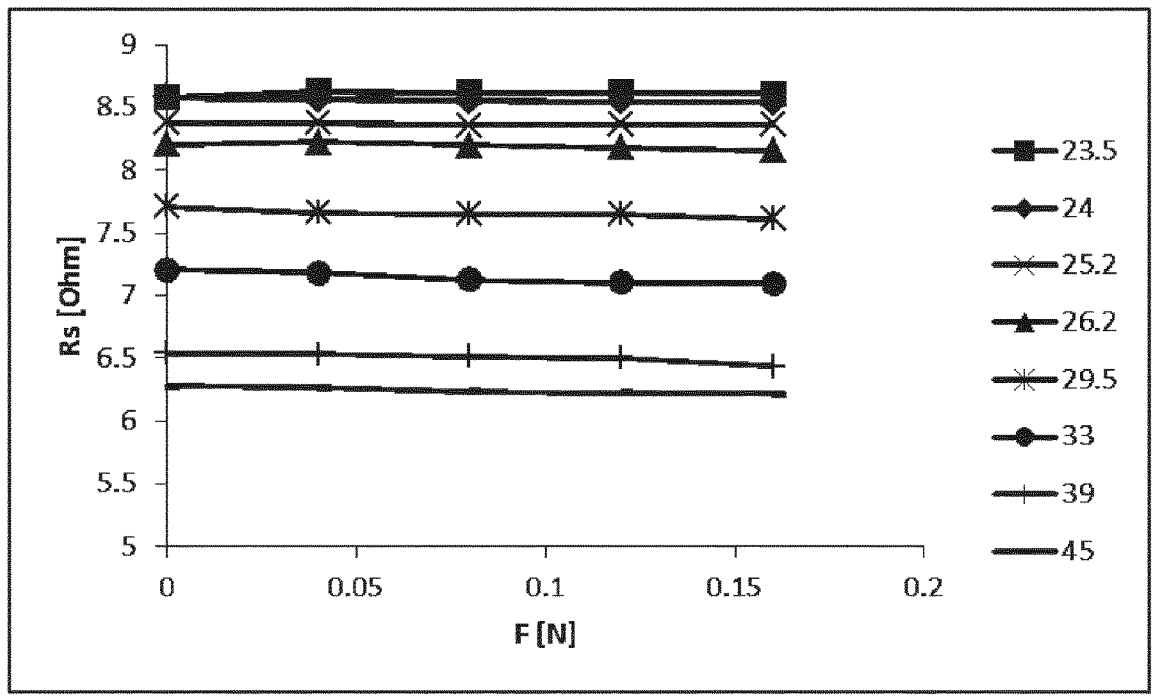
FIG. 13 shows the dependency the impedance on the load for different temperatures away from resonance.

At the second frequency (outside resonance coupling range) there is no influence of the electro mechanical coupling. At this frequency the resistance is only a function of temperature as shown in FIG. 13, which plots the resistance against the load. The resistance is plotted for the off resonance frequency (20 KHz) again measured for an actuator with 200V bias.

Figure 14:
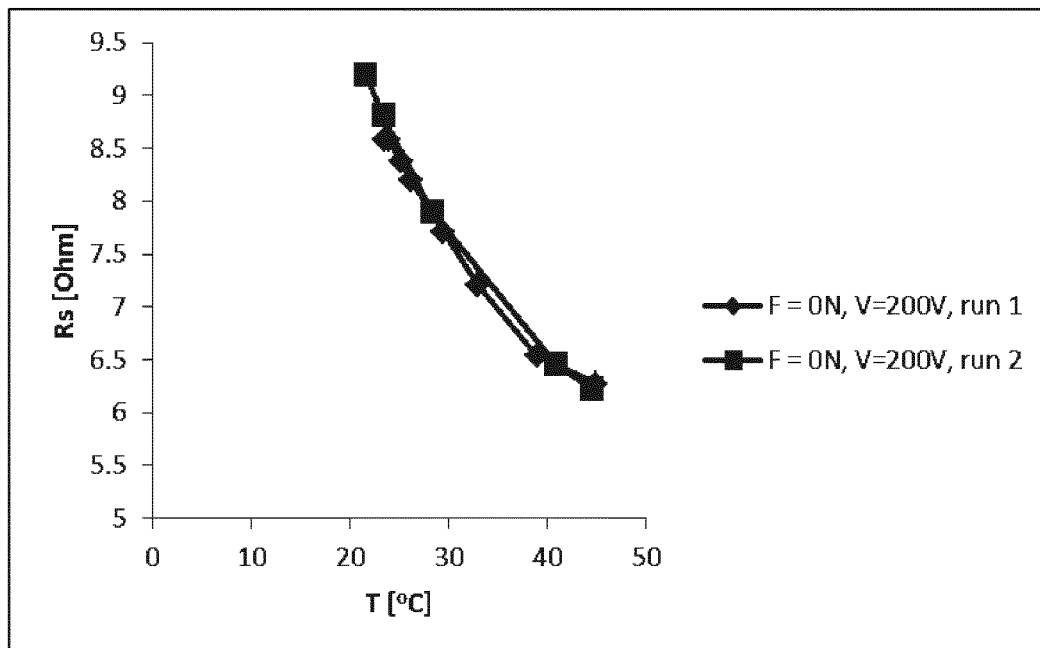
FIG. 14 shows the reproducibility of the temperature-impedance function.

The temperature offset drift is visible, but there is no influence from the applied load. As shown in FIG. 14, the temperature signal is reproducible because FIG. 14 plots the resistance versus the temperature for zero load, for two runs.

Figure 15:
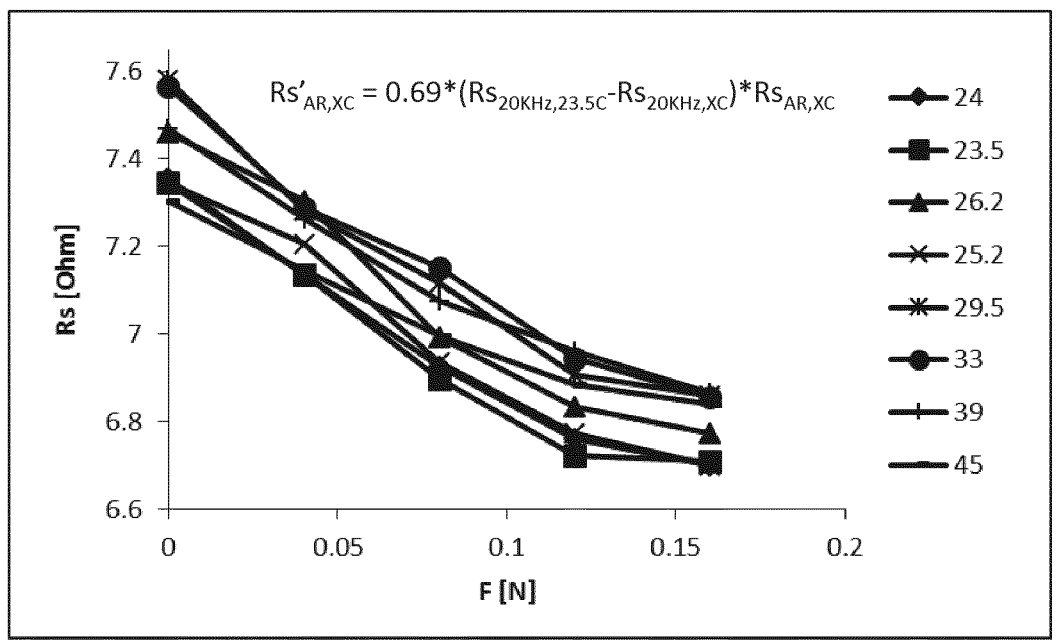
FIG. 15 shows how temperature compensation may be used to improve load sensing.

The temperature signal can also be used for compensation of the actuator signal, to improve the accuracy of the load sensor. In FIG. 15, the compensated resistance value as a function of load is given for 8 different temperatures from 23 to 45 degrees. The average difference between 23 degrees and 45 degrees is now 3.8% instead of 29% for non-compensated measurement.

The example above is based on a DC actuation signal. In a second example, there is a low frequency AC actuator signal. For low frequency AC actuation, the actuator is loaded electrically by a low frequency AC voltage and a small signal, high frequency AC voltage. The small amplitude, high frequency voltage is used for measurements and is superimposed on the low frequency AC actuator signal. The low frequency AC actuator voltage causes a deformation in the EAP which can be used for actuation purposes.

The low frequency actuation voltage preferably has a frequency at least 2 orders of magnitude (i.e. <1%) lower than the high frequency signal, to avoid interference of the actuator signal with the measurement signal.

In a third example, a frequency scan is not required to calibrate the system. This enables the system complexity and cost to be reduced. However, robustness and sensitivity can still be ensured. In production, the (anti-)resonance frequency ($f_r$) of an actuator will be tightly controlled so a predetermined set of 2 frequencies per temperature point within the temperature range is known a priori, thus a measurement at these two predetermined frequencies will always be indicative of load on the actuator (frequency 1) and temperature (frequency 2).

In a fourth example, a sensing device or an actuation and sensing device may be provided comprising a plurality of devices according to the above described examples, for example arranged in an array, or other desirable layout/shape. In examples, the plurality of devices may be provided such that each has a unique mechanical resonance frequency fr. In this way, on application of high frequency sensing signals to the array of devices, the characteristic (unique) resonance frequency of each device may be used to determine which actuator in the array is being stimulated as a sensor, i.e. to give the position of the sensor/actuator in the array.

For example, a common drive signal may be applied across all devices in the array, the common signal comprising a sequential series of signals of different frequencies (i.e. the known different resonance—or anti-resonance—frequencies of the devices). If the time-sweep of frequencies is faster than the sensor input, then a corresponding drop (or rise) in impedance will be detectable across the devices only for that frequency corresponding to the specific device which is stimulated, i.e. measured impedance will drop as the frequency sweep moves into fr corresponding to the stimulated device, and then rise again (or vice-versa) as the sweep moves out of fr. In such a system, $f_r$ (or Rs) can be used to identify which actuator is being used as a sensor i.e. to give the position of sensor/actuator in the array.

The example above makes use of impedance measurement to determine the applied load. Instead of detecting the (change of) the series resistance, the change in anti-resonance frequency may be detected to derive the corresponding feedback signal.

Alternatively, instead of detecting the (change of) the series resistance (or change in anti-resonance frequency) the change in phase may be determined, in particular the phase angle of the complex impedance. The change in series resistance Rs is relatively small. To improve sensitivity, it may be combined with another dependent variable.

Figure 16:
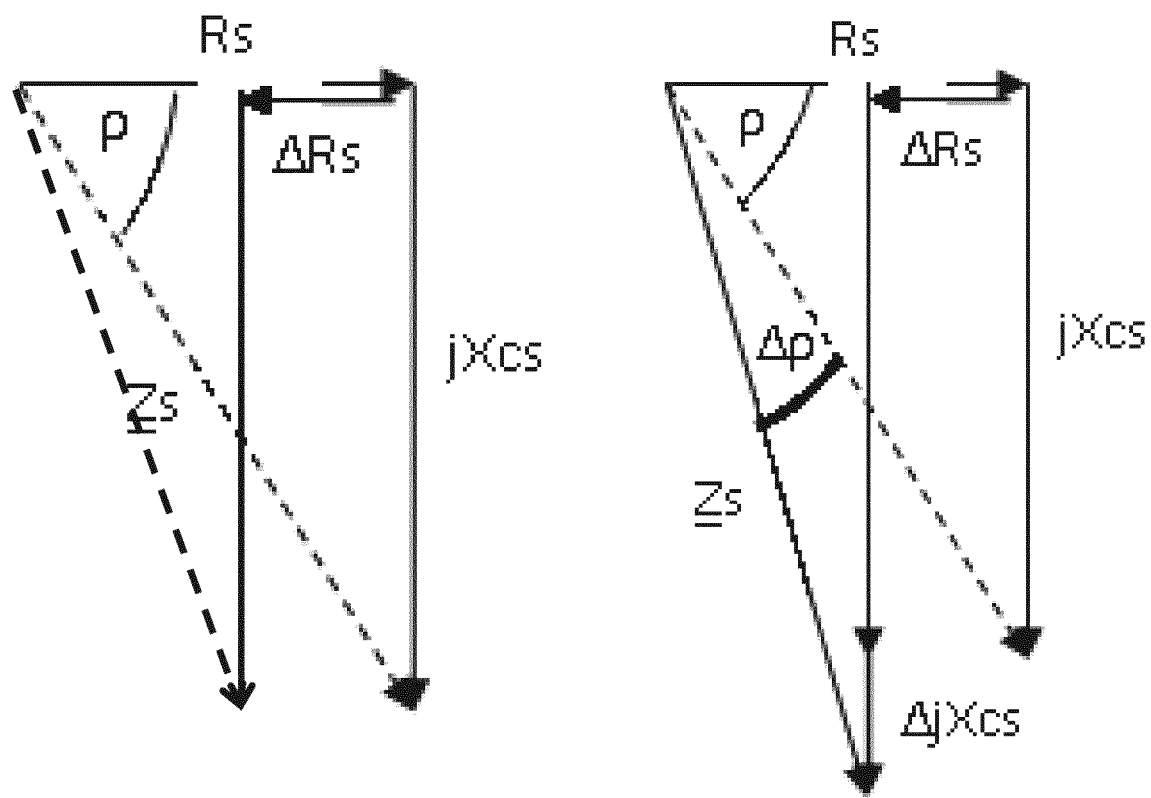
FIG. 16 is used to explain how phase measurements may be used.

In FIG. 16, a change in Rs is shown on the left, and a change in Cs and Rs is shown on the right.

The right image shows how the phase angle of the complex impedance changes by an increased amount (Δρ in response to a decrease in the real impedance part and an increase in the imaginary impedance part. The phase can be detected by measuring the change in phase between current and voltage. Especially, if EAPs have thin layers, the effect of changes in the imaginary part of the impedance (jXcs) may become dominant. Indeed, any measurements correlated to the complex impedance can be used to signify the loading of the actuator.

The sensitivity of the temperature sensing function may be tuned by suitable selection of the composition of the polymers (of the EAP actuator/sensor) used. The composition may be tuned to obtain the highest sensitivity of the sensor to the desired working temperature.

For example, in a (PVDF-TrFE-CTFE) polymer material, this can be achieved by varying the CTFE content.

Figure 17:
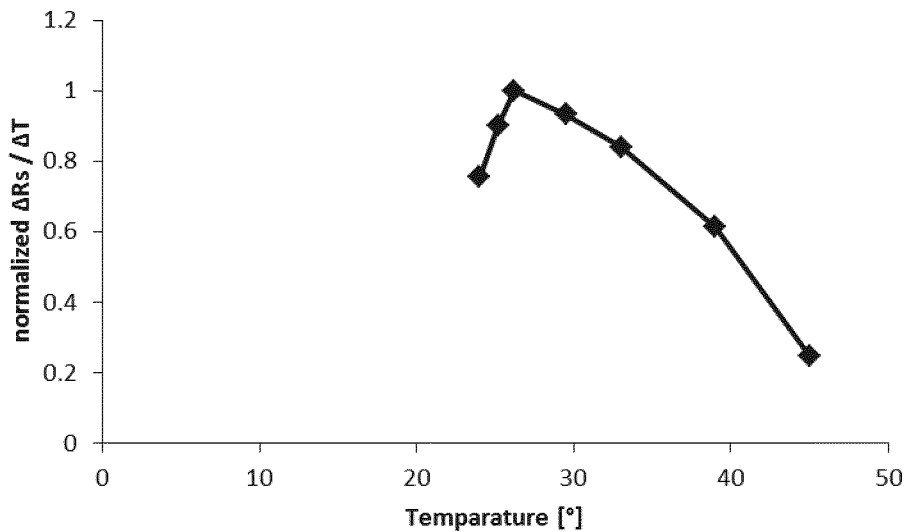
FIG. 17 shows the sensitivity of an example material with a certain composition versus temperature.

FIG. 17 shows the sensitivity of an example material (PVDF-TrFE-CTFE) with a certain composition versus temperature, and it shows a maximum sensitivity at 26 degrees Celsius. The example material has 10% CTFE content.

Figure 18:
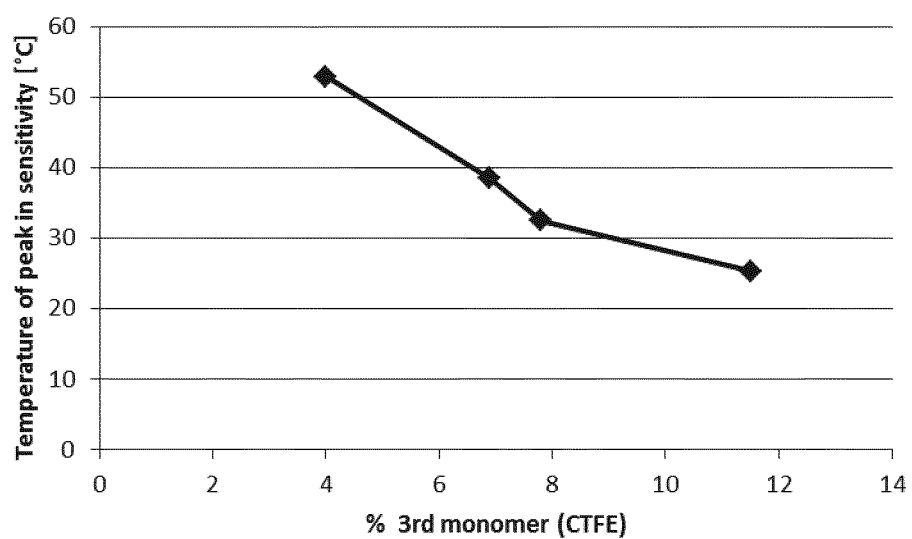
FIG. 18 shows the relationship between sensitivity and composition.

FIG. 18 shows the relationship between the suitable working temperature and CTFE content of the (PVDF-TrFE-CTFE) polymer, and shows the temperature at which the temperature sensitivity is highest versus the percentage of the CTFE content. As shown, a higher CTFE content gives rise to a reduced temperature at which the sensitivity is highest. For example a polymer with 7% CTFE may be used for in-body applications where the temperature is higher than for an indoor sensor at room temperature.

Materials suitable for the EAP layer are known. Electroactive polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behavior under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behavior of the EAP layer in response to an applied electric field.

The EAP layer of each unit may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

The invention can be applied in many EAP and photoactive polymer applications, including examples where a passive matrix array of actuators or sensors, or combined sensor and actuators is of interest.

The invention if of interest generally for load and temperature sensing. It may also be used when combined sensing and actuation functionality is needed.

In many applications the main function of the product relies on the (local) sensing and optionally also manipulation of human tissue, or the actuation of tissue contacting interfaces. In such applications EAP actuators for example provide unique benefits mainly because of the small form factor, the flexibility and the high energy density. Hence EAP's and photoresponsive polymers can be easily integrated in soft, 3D-shaped and/or miniature products and interfaces. Examples of such applications are:

Skin cosmetic treatments such as skin actuation devices in the form of a responsive polymer based skin patches which apply a constant or cyclic stretch to the skin in order to tension the skin or to reduce wrinkles;

Respiratory devices with a patient interface mask which has a responsive polymer based active cushion or seal, to provide an alternating normal pressure to the skin which reduces or prevents facial red marks;

Electric shavers with an adaptive shaving head. The height of the skin contacting surfaces can be adjusted using responsive polymer actuators in order to influence the balance between closeness and irritation;

Oral cleaning devices such as an air floss with a dynamic nozzle actuator to improve the reach of the spray, especially in the spaces between the teeth. Alternatively, toothbrushes may be provided with activated tufts;

Consumer electronics devices or touch panels which provide local haptic feedback via an array of responsive polymer transducers which is integrated in or near the user interface;

Catheters with a steerable tip to enable easy navigation in tortuous blood vessels.

Another category of relevant application which benefits from such actuators relates to the modification of light. Optical elements such as lenses, reflective surfaces, gratings etc. can be made adaptive by shape or position adaptation using these actuators. Here one benefit of EAPs for example is a lower power consumption.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A system, comprising:
an electroactive material sensor; and
a control system,
wherein the control system is arranged to perform measurements of an electrical characteristic,
wherein the electrical characteristic comprises an impedance or an impedance phase angle of the electroactive material sensor at least a first frequency and at a second frequency,
wherein the second frequency is different from the first frequency,
wherein the control system is arranged to derive, from the measurements, a temperature at the electroactive material sensor and an external pressure or force applied to the electroactive material sensor.

2. The system as claimed in claim 1, wherein the electroactive material sensor comprises a device which functions both as an actuator and as a sensor.

3. The system as claimed in claim 1, wherein the first frequency is a resonance frequency at which the electrical characteristic has a maximum or minimum value.

4. The system as claimed in claim 1, wherein the second frequency is a frequency at which the electrical characteristic is constant with respect to load.

5. The system as claimed in claim 1,
wherein the control system is arranged to apply a drive signal,
wherein measurement signals of the first and second frequencies are superposed on the drive signal, and
wherein the drive signal comprises a DC drive level.

6. The system as claimed in claim 1, further comprising an array of sensors, wherein at least some of the sensors have different first frequencies.

7. The system as claimed in claim 1, wherein the control system is arranged to modify the derived external force or pressure based on the derived temperature.

8. The system as claimed in claim 1, wherein the electrical characteristic comprises an impedance value.

9. The system as claimed in claim 1, wherein the electroactive material comprises a relaxor ferroelectric.

10. A method of using an electroactive material sensor comprising:
measuring an electrical characteristic,
wherein the electrical characteristic comprises an impedance or an impedance phase angle of the electroactive material sensor at least a first frequency and a second frequency, and
wherein the second frequency is different from the first frequency; and
deriving, from the electrical characteristic, a temperature at the electroactive material sensor and an external pressure applied to the electroactive material sensor.

11. The method as claimed in claim 10, wherein the first frequency is a resonance frequency, at which the electrical characteristic has a maximum or minimum value and the second frequency is a frequency at which the electrical characteristic is constant with respect to load applied.

12. The method as claimed in claim 10 further comprising applying a drive signal,
wherein measurement signals of the first and second frequencies are superposed on the drive signal,
wherein the drive signal comprises a DC drive level, and
wherein the electroactive material sensor comprises a device which functions both as an actuator and as a sensor.

13. The method as claimed in claim 10 further comprising modifying the derived external pressure based on the derived temperature.

14. The method as claimed in claim 10 further comprising performing a calibration operation,
wherein the calibration operation determines the first frequency and the second frequency, and
wherein the calibration operation comprises applying a first frequency sweep with no actuation signal and applying a second frequency sweep with an actuation signal.

15. The method as claimed in claim 10, wherein the electroactive material is chosen from the group consisting of organic electroactive materials and polymer electroactive materials.

16. The system as claimed in claim 1,
wherein the control system is arranged to apply a drive signal,
wherein measurement signals of the first and second frequencies are superposed on the drive signal,
wherein the drive signal comprises an AC drive signal, and
wherein the AC drive signal has a frequency below the first and second frequencies.

17. The system as claimed in claim 5,
wherein the measurement signals each have an amplitude of at most 10% of the amplitude of the drive signal.

18. The method as claimed in claim 10 further comprising applying a drive signal,
wherein measurement signals of the first and second frequencies are superposed on the drive signal,
wherein the drive signal comprises an AC drive signal,
wherein the AC drive signal has a frequency below the first and second frequencies, and
wherein the electroactive material sensor comprises a device which functions both as an actuator and as a sensor.

19. The system as claimed in claim 1, wherein the first frequency is an anti-resonance frequency.

20. A method of using an electroactive material sensor comprising:
measuring an electrical characteristic,
wherein the electrical characteristic comprises an impedance or an impedance phase angle of the electroactive material sensor at at least a first frequency and a second frequency, and
wherein the second frequency is different from the first frequency; and
deriving, from the electrical characteristic, a temperature at the electroactive material sensor and a force applied to the electroactive material sensor.

* * * * *